US006949351B1

(12) United States Patent
Squirrell et al.

(10) Patent No.: US 6,949,351 B1
(45) Date of Patent: Sep. 27, 2005

(54) CELL ASSAY, METHOD AND REAGENTS

(75) Inventors: David James Squirrell, Salisbury (GB); Melenie Jane Murphy, Salisbury (GB); Rachel Louise Price, Salisbury (GB)

(73) Assignee: The Secretary of State for Defence in Her Britannic Majesty's Government of the United Kingdom of Great Britain and Northern Ireland, Salisbury (GB)

( * ) Notice: Subject to any disclaimer, the term of this patent is extended or adjusted under 35 U.S.C. 154(b) by 0 days.

(21) Appl. No.: 10/009,292

(22) PCT Filed: May 9, 2000

(86) PCT No.: PCT/GB00/01771

§ 371 (c)(1),
(2), (4) Date: Nov. 13, 2001

(87) PCT Pub. No.: WO00/70082

PCT Pub. Date: Nov. 23, 2000

(30) Foreign Application Priority Data

May 13, 1999  (GB) .............................. 9911095

(51) Int. Cl.$^7$ ............................ C12Q 1/48; C12Q 1/66; C12Q 1/00; G01N 33/53

(52) U.S. Cl. ................................ 435/15; 435/8; 435/4; 435/975

(58) Field of Search .......................... 435/15, 8, 4, 975

(56) References Cited

U.S. PATENT DOCUMENTS 5,648,232 A  7/1997 Squirrell ..................... 435/34
5,798,214 A * 8/1998 Squirrell ..................... 435/7.4

FOREIGN PATENT DOCUMENTS

| EP | 0376189 | 7/1990 |
|----|---------|--------|
| WO | WO 94/17202 | 8/1994 |
| WO | WO 96/02665 | 2/1996 |
| WO | WO 96/02666 | 2/1996 |
| WO | WO 99/37799 | 7/1999 |
| WO | WO 99/41408 | 8/1999 |

OTHER PUBLICATIONS

Webster' II Dictionary; p446 and p749; (1984).*
Webster's Dictionary (1984).
T. Olsson et al., "Leakage of Adenylate Kinase from Stored Blood Cells", *Journal of Applied Biochemistry*, 5, pp. 437–445, (1983).

* cited by examiner

*Primary Examiner*—Louise N. Leary
(74) *Attorney, Agent, or Firm*—Kilpatrick Stockton LLP

(57) ABSTRACT

A method for detecting the presence of a lysed eukaryotic cell in a sample, said method comprising: (i) adding adenosine diphosphate (ADP) to said sample under conditions which allows the conversion of ADP to adenosine triphosphate (ATP) by cellular adenylate kinase, (ii) detecting ATP in said sample and relating that to the presence of adenylate kinase and thus to the presence of lysed cells. The method is useful in detecting the cell lysis, for example when screening for drugs which are required to cause lysis, for example for use in tumor therapy. However, in addition, cells may, in a preliminary step, be lysed and the contents quantitated in order to establish for example the health of condition of the cells or to detect the presence of cells in sample such as milk or urine, for diagnostic purposes.

9 Claims, No Drawings

CELL ASSAY, METHOD AND REAGENTS

This application claims priority to United Kingdom Patent Application No. 9911095.9 filed on May 13, 1999 and International Application No. PCT/GB00/01771 filed on May 9, 2000 and published in English as International Publication No. WO 00/70082 on Nov. 23, 2000.

The present invention relates to a method for detecting the presence of the contents of lysed eukaryotic cells, and to procedures which use this method. The method is useful in detecting the presence of such cells or monitoring the condition or integrity of cells in a preparation and has wide application for example, in the context of biochemical or pharmaceutical research, diagnosis or product screening.

All living organisms utilize adenosine triphosphate (ATP) as a source of chemical energy and it is known to assay this using the ATP driven luciferase/luciferin reaction. Light generated by this enzymic reaction can be measured using a luminemeter and related to the amount of ATP present. The usefulness of ATP as an index of microbial numbers has been known since the mid 1960's (see ATP Luminescence Rapid Methods in Microbiology (1989) editor Stanley et al.; Blackwell Scientific Publications, London see pages 1–10): its main advantage being speed and sensitivity. Utilizing this assay format, simple samples can be analysed in a matter of minutes while complex ones routinely take only half an hour with a detection capability provided down to $10^{-11}$ mol/l ATP.

It is known to assay adenylate kinase using the luciferase/luciferin system (see Brolin et al Journal of Biochemical and Biophysical Methods 1 (1979) 163–169) for the purpose of determining its activity in certain mammalian and plant tissues (Rodionova et al Fiziologiya Rastenii (1978) 25, 4, p 731–734 for plants).

The speed and sensitivity of the ATP based method for detecting microorganisms has been enhanced significantly by shifting the target of the assay from ATP to a particular enzyme which can be made to generate it, adenylate kinase (WO 94/17202 and WO 96/02665). Adenylate kinase is an enzyme used by all organisms for the interconversion of the adenylates, adenosine monophosphate (AM), adenosine diphosphate (ADP) and adenosine triphosphate (ATP). The reaction can be represented as $$ATP + AMP \leftrightarrows ADP$$

In the presence of an excess of purified ADP, the reaction can be driven towards the generation of ATP. Following deliberate lysis of the microorganism, for example by means of a detergent, a bioluminescent endpoint assay allows the detection the intracellular marker adenylate kinase.

The applicants have found a way of applying the technology to other fields, in particular to pharmaceutical or biochemical research and product screening.

In vitro cellular assays are widely carried out in laboratories exploring a wide range of diseases or investigating the effects of reagents or environmental conditions. In many of these assays, cell lysis is the "end point" which is to be detected. This is true for example in the detection of anticancer drugs where the effect of chemical or biochemical agents on tumour cells is of considerable interest. In such instances, the detection of screen leads may rely on lysis of relatively few cells within the culture. These leads may then be further optimised, for example by chemical modification.

A therapeutic target in many cases is to cause the death of cancer cells, either by necrosis or apoptosis. Abnormalities in cancer cells mean that they do not undergo normal programmed cell death or apoptosis. Thus some cancer therapies aim to induce apoptosis in cancer cells, as such therapies are less likely to damage healthy cells than cytotoxins.

Other assays which detect cell lysis include in-vitro toxicity testing to screen for cell damaging properties, or the detection of lytic viruses or bacterial toxins, such as verotoxin from *E. coli* 0157.

In other instances, the effects of a particular agent or environmental factor on the general condition of a cell is investigated. Even though a cell may not be lysed in the presence of a particular agent or set of environmental conditions, it may be affected in terms of its general condition and health and in particular, whether or not the cell is dividing and growing. Growth may be increased for example in the presence of a growth factor, but inhibited in the presence of agents or conditions which stress the cell. This type of assay is used for example, to screen for growth factors, to detect adverse effects for the screening for compounds intended to inhibit apoptosis, as may be required for therapeutic or diagnostic purposes.

At present, such assays generally require microscopic examination of the slide containing the cells to determine whether any cell lysis, for example as a result of apoptosis has occurred. This is time consuming and labour intensive. Alternative methods of detecting the end point include measuring the release of radioactive tracers, such as Cr*, which must be first introduced into the cell. Again this is time consuming and difficult and issues of safety when using radiolabelling are important.

In yet further cases, the detection of any cells in normally cell-free body fluids such as milk and urine, can be indicative of a disease state, such as mastitis. At present, these cell assays may be carried out various methods including microscopic examination of samples of the fluid, incorporation of radioactive thymidine into cells or enzyme assays which yield a colorimetric signal, more sensitive detection methods would assist in rapid and accurate diagnosis.

The present invention provides a method for detecting the presence of a lysed eukaryotic cell in a sample, said method comprising (i) adding adenosine diphosphate (ADP) to said sample under conditions which allows the conversion of ADP to adenosine triphosphate (ATP) by cellular adenylate kinase, (ii) detecting ATP in said sample and relating that to the presence of adenylate kinase and thus to the presence of lysed cells.

The samples used in the method will be eukaryotic cell preparations or samples suspected of containing eukaryotic cells. Cell preparations include cell cultures. As used herein, the expression "cell culture" refers to eukaryotic cells from a multicellular organism which are sustained in vitro. It includes tumour cell cultures hybridomas, recombinant cell lines and healthy tissue cell lines but excludes microorganisms.

When the cells undergo lysis in the culture medium, they release a cocktail of chemicals, including nucleotides, sugars and proteins which make up the cell. Both ATP and ADP found in the cell will be released but where the numbers of cells lysed is small, the amount of these components will be low. Detection of ATP under these circumstances will be difficult.

However, adenylate kinase released when a cell undergoes lysis catalyses the conversion of ADP to ATP in the presence of excess ADP. By introducing such an excess, adenylate kinase drives the equilibrium towards the generation of ATP, which is then present at sufficient levels to be detected and quantified. The signal generated from the sample is therefore amplified, allowing a much more sensitive screen to be implemented. This is particularly useful in the context of high throughput screening processes which used very small sample quantities. Standard 96 well microtitre plates are being replaced with plates with more wells, such as 384 and 1536 wells, which can hold proportionately less sample.

Suitably, the amount of ATP detected is related to the amount of free enzyme which can catalyse the conversion of ADP to ATP in said culture medium. This can be done by calculation or calibration methods as are conventional in the art.

Although adenylate kinase is present in smaller quantities than ADP or ATP, its use as a biological marker for cells provides enhanced sensitivity with a typical amplification available of 400,000 by measuring its presence through the ATP it produces; that is for every mole of enzyme present 400,000 moles of ADP are converted to ATP in a 10 minute incubation. Thus estimation of the enzyme by measuring the substrate or product of the reaction it catalyses provides for detection down to as low as $10^{-20}$ moles. The adenylate kinase content of a single mammalian cell is considerably greater than this.

Adenosine triphosphate (ATP) can be detected by a variety of conventional methods. Preferably it is detected by use of the luciferin/luciferase system which provides a photometrically detectable signal indicative of the amount of ATP in the sample. Luciferin/luciferase preparations and methods for their use in assaying ATP will be well known to those skilled in the art and are commercially available (e.g. see Brolin et al). A typical formulation contains e.g. 0.1 to 10 mg/liter luciferase, 15 to 1000 µmol/liter D-luciferin, and agents such as $MgCl_2$, EDTA, BSA, and pH7 buffer (see e.g. EP 054676).

The conversion of ADP to ATP requires the presence of magnesium ions. As all cells contain these ions to some degree the method of the invention does not essentially require their addition, but clearly their addition may be preferred in order to improve conversion rates and normalise reaction conditions such that samples deficient in magnesium can be assayed in a similar manner and give a signal comparable with samples replete in magnesium ions. Addition of magnesium ions increases the sensitivity and reliability of the assay.

The amount of magnesium present is preferably such that, even when account is taken of any chelating agent such as EDTA present, there is at least sufficient to provide one mole of magnesium for one mole of ADP such that all of the ADP molecules may be associated with at least one magnesium ion.

In particular, the method can be used to monitor cell integrity in a cell preparation, for example a cell culture. As mentioned above, there are a variety of screening methods where the endpoint is cell lysis, which may utilise the method of the present invention. In these methods, a cell culture under investigation is incubated under test conditions for a suitable period to ensure that any lysis which is occurring as a result of those test conditions takes place.

Test conditions will depend upon the nature of the assay being carried out. They may include the presence of agents such as chemical (organic or inorganic), biological or biochemical reagents as well as temperature, pH, pressure, irradiation or other environmental factors which could impact on cell viability. In particular however, the sorts of conditions which may give rise to cell lysis in culture include the addition of agents such as chemicals or biochemicals including peptides, proteins and viruses, which are suspected of having a lytic effect on cells. They may be targeted at particular cell types such as tumour cells, and may be intended for use in anti-cancer therapies.

Using the method of the invention, a wide range of chemicals can be screened rapidly and sensitively, using robotic techniques if required ADP and preferably also magnesium ions are added to a cell culture, which may then further incubated under conditions which will allow target enzymes such as adenylate kinase present to convert ADP to ATP. At that point, detection agents such as luciferase and luciferin agents are added and any resultant light signal detected and/or quantitated. If necessary, this can then be related to presence and/or amount of adenylate kinase and thence to the degree of cell lysis in the sample, either by calculation or calibration, or by comparison with a control sample which has not been subjected to the test conditions and a control sample to which a lytic agent, which can release 100% of adenylate kinase, has been added.

This method is particularly suitable for use in the screening of compounds for pharmaceutical application. For example, where the cell preparation is a tumour cell line, reagents suspected of having anti-cancer applications can be applied. The presence of lysed cells in the preparation following the method of the invention indicates that the reagents are killing tumour cells.

Thus in a preferred embodiment the invention provides a method of screening reagents for the induction of cell lysis in tumour cells, said method comprising incubating tumour cells in the presence of said agent, and detecting cell lysis using the method described above.

Alternatively, the effect of chemicals on normal cells may be assessed using this method. Such information may be of assistance in determining the toxicity of such compounds and therefore the method in useful in in vitro toxicology.

The method may also be used in diagnosis, for example, where a patient is suspected of suffering from a viral infection which causes lysis such as polio.

In this case, a sample such as a serum sample, from a patient suspected of suffering from viral infection is added to cells in culture. The detection of lysed cells in the resultant cell culture would be indicative of the presence of viral infection in the patient.

The method may however, be modified to allow the condition of eukaryotic cells in a sample to be monitored. In this case, a sample of eukaryotic cells which have been incubated under test conditions, such as those outlined above, are subject to a preliminary step in which they are lysed. This can be effected by a variety of known methods, including the application of energy sources, but can conveniently comprise the addition of a lytic agent such as a detergent. Once cells in the sample have been lysed, the quantity of ATP is detected and this is used to quantify the amount of adenylate kinase present in the cells. The adenylate kinase content of a cell equates to its cell mass, which is indicative of whether a cell is growing and/or dividing normally. Thus, this embodiment can be used to determine the condition of the cells. In the context of the application, the "condition" of cells refers to their health and in particular, whether they are growing and dividing normally.

Test conditions under which the cell cultures are incubated may, as before, comprise the addition of a an agent such as a chemical (organic or inorganic), biochemical or biological agent, for example during the screening of agents for growth factor activity. However, the effects of environmental factors such as temperature, pH, pressure, irradiation or the presence of a particular gaseous environment on the condition of cells may also be investigated using this method.

In yet a further embodiment, the method of the invention may be used to detect the presence of eukaryotic cells in a sample, for example of body fluids such as urine or milk, which in a healthy individual, are cell-free. The method of the invention allows the detection of even small numbers of cells in these fluids, thus giving the possibility of early diagnosis of diseases such as mastitis. In this case also, a sample of fluid will be subject to a preliminary step, in which cells in the sample are lysed to release their content.

In a particular embodiment of the invention, the signal generating luminometry reagents such as luciferase/luciferin are added to the sample at the beginning of the incubation, preferably at the same time and preferably in admixture with with the ADP and any magnesium ion source.

As with any amplifying kinase, the sensitivity of the assay of the present invention is limited by the purity of the reagents. In this case the significant contaminants may be ATP in the ADP substrate and enzymes such as adenylate kinase in the luciferase preparations, particularly where these are stabilised for example using bovine serum albumin (BSA). For use as a sensitive assay for cell lysis, it is necessary that the purity of each of the reagents be as high as possible with respect to the substance which is to be assayed and with which it is to react in the assay.

As described in WO 94/17202 and WO 96/02665, high purity commercial ADP (>99.5% purity) is preferably used only after further purification by column chromatography. Examples of suitable column chromatography methods are also described. Methods for obtaining ADP with a molar % ATP upper limit of $2 \times 10^{-8}$ are described.

A further method for removing ATP from the ADP substrate uses enzymes that specifically degrade ATP, such as luciferase or apyrase. Such enzymes may also be used to further purify chromatographically purified ADP, or alternatively enzymically purified ADP may be treated by column chromatography. It will be noted that apyrase is also an ADPase, but as some apyrases are more active on ATP and ADP is present at much higher levels this does not present a significant problem.

Various methods for eliminating troublesome contaminating enzymes such as adenylate kinase from luciferase preparations as well as BSA which may be used as a stabiliser in these preparations are set out in WO 94/17202 and WO 96/02665. These include size exclusion chromatography, reverse phase chromatography or simply leaving the luciferase to stand for a period of months or years so that the unwanted enzymes degrade.

Methods of producing enzymes such as luciferase which are free or substantially free of contaminating enzymes such as adenylate kinase are described in co-pending International No PCT/GB98/0304. In summary, in accordance with this process, the luciferase enzyme is produced using recombinant DNA technology. A host cell such as a bacterial cell, is transformed so that it expresses the desired luciferase enzyme and also the contaminating enzyme in a mutant form which is functional to allow the host cell to proliferate. However, the mutant form of the contaminating enzyme such as adenylate kinase is designed to be unstable under certain conditions, for example of temperature, at which the luciferase remains stable. Once the luciferase has been recovered from the host cell culture, it is subjected for a sufficient period of time to the conditions such as temperature, under which the contaminating enzyme is unstable so that it is denatured.

Suitably the reaction conditions used in the method of the invention will be broadly similar to those described in WO 94/17202 and WO 96/02665. Suitably, ADP is added such that the ADP concentration lies between 0.005 mM and 1 mM and preferably in excess of 0.08 mM. A particularly preferred amount of ADP in the conversion step mixture is about 0.1 mM.

Suitably the concentration of magnesium ions in the culture is at least 1 mM, more preferably 5 mM or more and most preferably 10 mM or more, for example from 10 to 30 mM. Higher concentrations will be preferred where reagents are to be used in the assay or in the cell culture which contain magnesium ion depleting agents, e.g. chelating/sequestering agents such as EDTA and phosphate buffers, it will be preferable that an excess of magnesium ions is present in order to maintain good conversion rates.

The magnesium ions may be provided in the form of any magnesium salt, preferably as magnesium acetate.

Luciferase is preferably stored separately from extractant.

As $Mg^{2+}$ ions facilitate ADP depletion by contaminant adenylate kinase, it is preferred not to keep them in solution together prior to use; chelating agents such as EDTA may be included in the ADP to prevent this. Preferably the magnesium and ADP are brought together just prior to use or in the ADP conversion step. Where the reagents are to be kept together it is preferred that they are kept in freeze dried form to avoid any premature ADP conversion to ATP.

When ADP and luciferase/luciferin are administered in a single reagent, it is preferred that the reagent pH is adjusted to that which is suitable for both enzymes. This will allow counting to continue while converting ADP to ATP. Suitable pH values may be determined by routine experiment using known cell numbers in a sample with known lytic agents. The sample, ADP and magnesium ion source may be mixed in any buffer providing a pH suitable for the adenylate kinase reaction; no other reagents are necessary. Thus any buffer providing a pH of between 5.5 and 8.5 might be used, with optimal pH lying between pH6 and 7, preferably pH6.5. Examples of suitable buffers include Tris and phosphate buffers. Most suitably the sample is collected and/or diluted in such a buffer in preparation for carrying out the method of the invention.

The light given off from the mixture after all the steps are complete, i.e. ADP conversion to ATP and subsequent action of luciferase upon luciferin, may be measured by residence of the sample volume, e.g. luminometer tube, within a light detector immediately after or simultaneously with addition of the luciferase and luciferin or other agents which enable the essential steps to proceed.

In yet a further aspect of the present invention there is provided a test kit for performing the method of the invention. The test kit of the present invention comprises the essential reagents required for the method of the invention, i.e. adenosine diphosphate together with luciferase and luciferin, and cell culture medium. It may also contain a magnesium ion source. The kit is suitably in the form of a single package preferably including instructions as to how to perform the method of the invention; the reagents being provided in containers and being of strength suitable for direct use or after dilution. Phosphate buffer may be included.

Apparatus for performing the method of the invention will be similar to that describe in WO 94/17202 and WO 96/02665. In this case however, the sample holding means will suitably comprise an incubation vessel, microtitre plate or slide. This may be subject to heating to ensure that the cell culture is maintained at a temperature at which cells are actively growing and dividing in order to ensure that no false positives are generated by cell death from causes other than the condition under test.

Other features of the apparatus used in the method of the invention include means for addition of ADP, magnesium ions where appropriate and the detection agents such as luciferase and luciferin to the cell culture and means for detecting a signal such as light produced.

The apparatus will typically include a detection means for determining the amount of light emitted from the suspension on addition of the luciferase and luciferin and optionally includes a computer processor and visual display unit for receiving a signal for the detection means indicative of the amount of light emitted and for calculating from that the likely presence and amount of lysed cells in the culture and displaying results. Such calculation might be facilitated by programming the processor to take account of a set order of incoming signals, some of which will be controls including blank and nonionic detergent runs, or take account of pre-input standards e.g. temperature.

What is claimed is:

1. A method for determining whether a reagent which is suspected of having a pharmaceutical activity has an effect on eukaryotic cell integrity, the method comprising
   (i) adding the reagent to a cell culture and incubating the cell culture for a period of time sufficient to allow the reagent to cause cell lysis,
   (ii) adding adenosine diphosphate (ADP) to the cell culture under conditions which allow the conversion of ADP to adenosine triphosphate (ATP) by cellular adenylate kinase, and
   (iii) detecting ATP in the cell culture and relating the amount of ATP detected to the presence of adenylate kinase and thus to the eukaryotic cell integrity.

2. The method of claim 1, wherein the cell culture is a tumor cell line in culture medium and the reagent is suspected of having anti-cancer applications.

3. The method of claim 1, which is used in toxicity testing.

4. A method for determining whether a reagent has an effect on the growth of eukaryotic cells, the method comprising
   (i) adding the reagent to a cell culture and incubating the cell culture for a period of time sufficient for the reagent to affect the growth of the cell culture;
   (ii) lysing cells in the cell culture;
   (iii) adding adenosine diphosphate (ADP) to the cell culture under conditions that allow the conversion of ADP to adenosine triphosphate (ATP) by cellular adenylate kinase; and
   (iv) detecting ADP in the cell culture and relating the amount of ATP detected to the condition of the cells.

5. The method of claim 4 wherein the initial cell culture contains a known amount of cells.

6. The method of claim 4 wherein the reagent is a compound that is being screened for growth factor activity.

7. The method of claim 4, wherein the cells are lysed by addition of a lytic agent.

8. A test kit for performing a method according to claim 1, which comprises substantially pure ADP, detection reagents and cell culture medium.

9. The test kit of claim 8 wherein the detection reagents are luciferase/luciferin, which is substantially free of contaminating enzymes.

* * * * *